United States Patent [19]

Muntwyler

[11] 4,290,846
[45] Sep. 22, 1981

[54] METHOD OF PROTECTING ORGANIC OR INORGANIC MATERIAL FROM ATTACK BY MICROORGANISMS

[75] Inventor: Rene Muntwyler, Hofstetten, Switzerland

[73] Assignee: Ciba-Geigy Corporation, Ardsley, N.Y.

[21] Appl. No.: 62,193

[22] Filed: Jul. 30, 1979

[30] Foreign Application Priority Data

Aug. 8, 1978 [CH] Switzerland ............... 8472/78

[51] Int. Cl.$^3$ ............................................. D21D 3/00
[52] U.S. Cl. ........................... 162/161; 106/18.35; 424/347; 427/369; 427/371; 427/428; 427/430.1; 427/434.2; 427/435; 427/439; 427/440
[58] Field of Search ............ 427/369, 371, 428, 430.1, 427/434.2, 435, 439, 440; 106/18.35; 210/62; 424/347

[56] References Cited

U.S. PATENT DOCUMENTS

| | | | |
|---|---|---|---|
| 3,400,201 | 9/1968 | Mocotte | 106/18.35 X |
| 3,417,185 | 12/1968 | Herschler | 210/62 X |
| 3,777,022 | 12/1973 | Cantor | 424/347 X |

*Primary Examiner*—Bernard D. Pianalto
*Attorney, Agent, or Firm*—Edward McC. Roberts; John P. Spitals

[57] ABSTRACT

The invention discloses a method of protecting organic or inorganic material from attack by microorganisms, which comprises incorporating in or applying to the surface of the material to be protected 3,5-dibromo-4-chlorophenol, 3,5-dibromo-4-fluorophenol or 3,5-dichloro-4-bromophenol or a mixture thereof. Compositions for carrying out the method of the invention are also disclosed.

12 Claims, No Drawings

METHOD OF PROTECTING ORGANIC OR INORGANIC MATERIAL FROM ATTACK BY MICROORGANISMS

The present invention relates to a method of protecting organic or inorganic material from attack by microorganisms by treating said material with trihalophenols, and also to compositions for carrying out this method which contain those compounds.

Numerous di- and polyhalophenols, their effectiveness against different microorganisms and their use as germicides and preservatives are known from the literature (cf. for example U.S. Pat. Nos. 3,033,746, 3,062,710, 3,215,596 and 3,417,185, British Pat. specification No. 980,254, Japanese patent publications Nos. 29015/68 and 53-26303, German Auslegeschrift No. 1 160 140, German Offenlegungsschrift No. 2 607 349, Journal of the Scientific Research Institute, Vol. 48 (1954) 38–48, Archives of Biochemistry 40 (1952) 306–309, Chemical Reviews 28 (1941) 269). All the halophenols described hitherto either have serious deficiencies in their activity spectrum, are unsuitable for individual substrates, have too high a toxicity or an unpleasant odour, are difficult to obtain, require a high concentration, or for other reasons cannot be used in practice or are of only limited utility.

The present invention is based on the surprising observation that 3,5-dibromo-4-chlorophenol, 3,5-dibromo-4-fluorophenol and 3,5-dichloro-4-bromophenol have an excellent antimicrobial action, that they do not have many of the disadvantages of the known halophenols, and that they are therefore most suitable for protecting organic and inorganic material, preferably textiles made from natural fibres, technical formulations, paper making slurries, industrial recirculating water systems, wood, oils etc., from attack by microorganisms, in particular fungi, and thus also for protecting said material from rot and mildew.

The method of the present invention comprises incorporating in, or applying to the surface of, the organic or inorganic material to be protected, 3,5-dibromo-4-chlorophenol, 3,5-dibromo-4-fluorophenol or 3,5-dichloro-4-bromophenol, or mixtures thereof.

Of the three halophenols eligible for use in the method of the invention, 3,5-dibromo-4-chlorophenol and 3,5-dichloro-4-bromophenol are preferred. 3,5-Dibromo-4-chlorophenol is particularly preferred.

The present invention also provides compositions for carrying out the method of the invention which contain a specific amount of trihalophenol compound. Depending on the end use, these compositions can contain different assistants and solvents. The trihalophenol compounds which can be used in the method of the invention are readily soluble in organic solvents and in propellant gases for aerosols. The compositions can therefore contain such solvents and propellant gases if it is desired to spray or apply them to surfaces.

The water-soluble salts of the eligible halophenols are also effective and are of particular importance where an application in aqueous medium is contemplated. Aqueous compositions can also contain the free phenols. Further assistants which the compositions of the invention may contain are listed in the survey provided hereinafter of the fields of use in which the method according to the invention can be employed and in the Examples.

Examples of such assistants are: anionic wetting agents, such as soaps, benzenesulfonates, cationic wetting agents, such as alkylargyl sulfate, nonionic wetting agents, such as polyglycol ethers and higher fatty alcohols, chelating agents, such as sodium hexamethaphosphate, aromatic substances, plasticisers, softeners, fillers, such as silicates, carbonates and/or finishing agents or starch derivatives.

In general, the compositions of the invention can be in the form of solutions, sprays, dispersions or emulsions.

The trihalophenol compounds eligible for use in the present invention possess a broad antimicrobial activity spectrum and exhibit both microbistatic and microbicidal action. Good action is observed against both gram-positive and gram-negative bacteria and algae and, in particular, against fungi. With regard to the technical aspects of their use, the lack of colour and freedom from odour of the compounds are of particular importance.

In accordance with the broad activity spectrum of 3,5-dichloro-4-bromophenol, 3,5-dibromo-4-chlorophenol and 3,5-dibromo-4-fluorophenol, the method of the invention for protecting a great variety of organic and inorganic substrates can be employed in a wide field of technology and industry, in particular for preserving and disinfecting industrial products and rendering them resistant to microorganisms and rot. The protection of various materials of organic origin from rot induced by bacteria and fungi is to be singled out for mention. The outstanding action of the compounds employed in the method of the invention against fungi is to particularly highlighted. In this field especially they are superior to the known similar halophenols of the prior art. For this reason, it is particularly preferred to employ the method of the invention in all those fields of use in which an action against a wide variety of fungi is necessary (e.g. protection against rot, mildew etc.). A number of principal fields of use are listed hereinafter.

An important field of use is the preservation of technical formulations, for example: adhesive substances, binding agents, paints, textile assistants and finishing agents, colour pastes and printing pastes, lacquers and similar preparations based on organic and inorganic dyes and pigments, also those which contain casein or other organic compounds. Wall and ceiling paints, for example those which contain an albuminous binder, are also protected from attack by pests by the method of the invention. Other uses to be mentioned are: the preservation of water base glues, for example of wallpaper pastes, especially from attack by fungi, the prevention and control of bacteria and fungus infections in animal oils, fats and emulsions, such as cutting oils, boring oils. When preserving paints and lacquers by the method of the invention, the coats and finishes obtained therewith are also protected in particular from attack by fungi. It is also possible to protect plasticisers, permanent sizes (e.g. based on polyvinyl alcohol) or starch sizes. Plastics moulding compounds of all kinds, e.g. derived from polyamides, polycarbonates, polyesters, polyvinyl chloride, polypropionate or polyvinyl alcohol, are also advantageously protected from attack by bacteria and fungi by the method of the invention. When using plasticisers, it is advantageous to add the antimicrobial agent to the moulding compound dissolved or dispersed in the plasticiser. It is expedient to ensure as uniform a distribution in the moulding compounds as possible. The treated moulding compounds can be used to obtain commodities of all kinds in which it is desired to effect an action against bacilli of the most diverse kinds, for example bacteria and fungi, thus, for example, in foot mats, bathroom curtains, seating accomodation, drip channel grating in swimming baths and wall hangings. By incorporating the trihalophenol compounds employed in the method of the invention in corresponding wax compositions and floor polishing pastes, there are obtained floor and furniture polishes with disinfectant action.

To bring about the desired effect, the trihalophenol compound is mixed with the above mentioned substrates and formulations and distributed therein as homogeneously as possible. The compound can be employed by itself in the appropriate amount, or dissolved, dispersed or emulsified in a solvent or dispersant which may additionally contain further assistants, e.g. dispersants or emulsifiers. The concentration of trihalophenol compound should be at least 100 ppm, based on the material to be protected. For practical purpose, the concentration will be about 100 to 10,000, preferably 200 to 5000, ppm.

The method of this invention is used with advantage for providing fibres and textiles with a preservative and disinfectant finish. The compounds suitable for use in the method of the invention are applied to natural and synthetic, preferably natural, fibres, on which they exert a lasting action against harmful (also pathogenic) microorganisms, e.g. fungi and bacteria. The compounds can be added before, simultaneously with or after a treatment of these textiles with other substances, e.g. colour or printing pastes, flame retardants, fabric softeners and other finishing agents. Textiles thus treated are protected against rot induced by microorganisms.

The formulations in which the compounds suitable for use in the method of the invention are applied may correspond to those conventionally employed in the art.

The compositions used for finishing and protecting textiles should contain the trihalophenol compounds in a finely divided form. In particular, solutions, disperions and emulsions of these compounds are therefore used. Aqueous disperisons can be obtained, for example, from pastes or concentrates, and can be applied as liquids or in aerosol form.

The aqueous solutions or dispersions advantageously contain surfactants, for example anionic compounds such as soaps and other carboxylates (e.g. alkali metal salts of higher fatty acids), derivatives of sulfuroxyacids (e.g. sodium salt of dodecylbenzenesulfonic acid, water-soluble salts of sulfuric acid monoesters of higher molecular alcohols or of their polyglycol ethers, for example soluble salts of dodecyl alcohol sulfate or of dodecyl alcohol polyglycol ether sulfate), derivatives of phosphorus-oxyacids (e.g. phosphates), derivatives with acid (electrophilic) nitrogen in the hydrophilic group (e.g. disulfine salts), cationic surfactants, such as amines and their salts (e.g. lauryldiethylenetriamine), onium compounds, amine oxides or nonionic surfactants, e.g. polyhydroxy compounds, suffactants based on mono- or polysaccharides, higher molecular acetylene glycols, polyglycol ethers (e.g. polyglycol ethers of higher fatty alcohols, polyglycol ethers of higher molecular alkylated phenols). In addition, the liquor can also contain conventional assistants, for example water-soluble perborates, polyphosphates, carbonates, silicates, fluorescent whitening agents, plasticisers, acid reacting salts, e.g. ammonium- or zincsilicofluoride, or certain organic acids, e.g. oxalic acid, and also finishing agents, e.g. those based on synthetic resin or on starch.

The textiles can be impregnated with the suitable active compounds e.g. by means of hot or cold dyeing, bleaching, chroming or aftertreatment baths, in which connection various textile finishing processes are suitable, e.g. the pad or exhaust method.

The treatment is expediently carried out in the temperature range between 10° and 100° C., for example between 10° and 70° C., but preferably at about room temperature.

On account of their good solubility in organic solvents, the active compounds are also very suitable for application from non-aqueous media. The material to be finished and protected can in this case simply be impregnated with the solutions.

Examples of suitable organic solvents are trichloroethylene, methylene chloride, hydrocarbons, propylene glycol, methoxyethanol, ethoxyethanol and dimethyl formamide, to which may also be added dispersing agents (e.g. emulsifiers, such as sulfated castor oil and fatty alcohol sulfates), and/or other assistants.

Depending on the end use, the contend of trihalophenol employed as active compound in the method of the invention can be, for example, between 0.1 and 50 g, preferably between 1 and 30 g, per liter of treatment liquor.

In the method of this invention, the active compounds can be used by themselves, or together with other known antimicrobial textile protectants.

Suitable textiles to be finished and preserved are both fabrics of natural origin, such as cellulosic fabrics, e.g. cotton, or polypeptide-containing fabrics, e.g. wool or silk, and fabrics of synthetic origin, such as those based on polyamide, polyacrylonitrile or polyester, as well as blends thereof.

The amount of trihalophenol compound applied to the textiles is preferably at least 100 ppm, based on the weight of the material.

In general, the textiles are adequately protected against infestation by fungi and bacteria by an amount of 100 to 5000 ppm, preferably 200 to 2000 ppm, of active compound, based on the weight of the material.

Detergents and cleansing agents having excellent antibacterial or antimycotic action are obtained by combining the suitable trihalophenol compounds with surface-active substances, especially with active detergents.

The detergents and cleansing agents can be in any desired form, e.g. in liquid, pasty, solid, flake or granular form. The suitable trihalophenol compounds can be incorporated in anionic compounds such as soaps and other carboxylates (e.g. alkali metal salts of higher fatty acids), derivatives of sulfuroxyacids (e.g. sodium salt of dodecylbenzenesulfonic acid, water-soluble salts of sulfuric acid monoesters of higher-molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), as well as into cationic surface-active agents, such as amines and their salts (e.g. lauryldiethylenetriamine), onium compounds, amine oxides or nonionic surface-active agents, such as polyhydroxy compounds, surface-active agents based on mono- or polysaccharides, higher-molecular acetylene glycols, polyglycol ethers (e.g. polyglycol ethers of higher fatty alcohols, polyglycol ethers of higher-molecular alkylated phenols), or in mixtures of different surfactants. The antimicrobial activity of the halophenol compounds is at the same time completely retained. The content of active compound in the detergents and cleansing agents, based on the weight of these agents, is from 0.1 to 20%, generally 0.1 to 3%. Aqueous preparations of such detergents and cleansing agents containing trihalophenol compounds suitable for use in the method of the invention can be employed e.g. for providing textiles with an antimicrobial finish. They are also suitable as antimicrobial cleansing agents in the food manufacturing and bottling industries, e.g. in breweries, dairies, cheese dairies and slaughterhouses.

The method of the invention can furthermore be employed for protecting a very wide variety of surfaces from attack by bacteria and fungi. Particular mention in this connection may be made of the treatment of wood (as raw material), articles made from wood, wood shavings, sawdust, leather, hides and pelts. The method of the invention can also be employed for disinfecting and protecting containers for e.g. technical formulations, floors, walls and fittings in stables and slaughterhouses. Depending on the shape of the object to be protected, the above mentioned objects or surfaces are sprayed, coated or impregnated (e.g. wood and leather) with an aqueous or organic solution or dispersion which contains the active compound.

Examples of suitable organic solvents are water-immiscible solvents, in particular petroleum fractions, and also water-miscible solvents such as lower alcohols (e.g. ethanol and methanol), ethylene glycol monomethyl or monoethyl ether.

Preferably, the composition is applied in an amount such that the respective object, after treatment, contains about 0.1 to 10 g/m² of active compound. In the treatment of wood it is possible, in particular, to prevent or delay the discolouration and rot caused by different fungi during storage.

The method of the invention can also be employed in the paper industry, where in particular the formation of slime caused by microorganisms in the machinery used for manufacturing paper is prevented. To this end, the active compound is added either to the pulp or to recirculating water system in the paper factory. The method of the invention can also be employed in analogous manner in other industrial plants where contamination by microorganisms is to be expected. The concentration of active compound will usually be at least 100 ppm, in practice about 100 to 10,000 ppm and preferably 200 to 5000 ppm. When adding active compound to recirculating water systems, a concentration of about 10 ppm often suffices.

In the method of the invention, the trihalophenols suitable for use as active compounds can also be combined with other disinfectants and preservatives, when frequently the action is potentiated. Mention may be made in this connection of combinations with other phenol derivatives, aldehydes (e.g. formaldehyde, salicylaldehyde), alcohols, carboxylic acids and derivatives thereof, organometallic compounds (e.g. tributyl tin oxide), halogens and halogen compounds (e.g. chlorine and iodine compounds), carbonic acid derivatives (e.g. dimethyl dicarbonate or diethyl dicarbonate), amines and quaternary ammonium compounds, phosphonium compounds, sulfonium compounds and heterocyclic compounds (e.g. halogenated and/or quaternated pyridine derivatives).

The 3,5-dibromo-4-chlorophenol employed in the method of the invention is known from an article by M. Kohn et al. in Monatshefte der Chemie 47 (1927), 207–240, and 3,5-dibromo-4-fluorophenol is mentioned in an article by L. M. Epshtein et al., Bulletin of the Academy of Sciences of the USSR 1975, 2334-9. 3,5-Dichloro-4-bromophenol is mentioned as intermediate by W. S. Gump et al., in J. Soc. Cosmetic Chemists 15, 717 (1964).

3,5-Dibromo-4-chlorophenol and 3,5-dibromo-4-fluorophenol can be obtained by different methods:

(1) By the method described by M. Kohn et al. (Monatshefte der Chemie 47 (1927), 207–240) according to the reaction scheme:

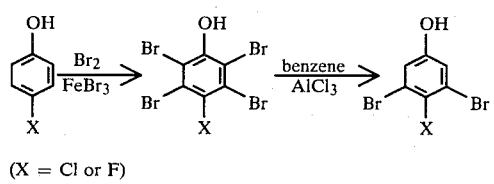

(X = Cl or F)

(2) 1st step as in (1); cathodic debromination by the method of M. Busch et al., Chem. Berichte 70 (1937), 744:

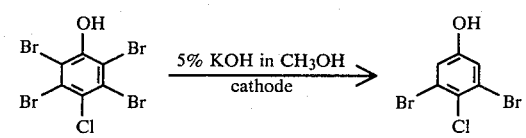

or debromination by the method of H. Hoffman et al., Chem. Berichte 95 (1962), 523:

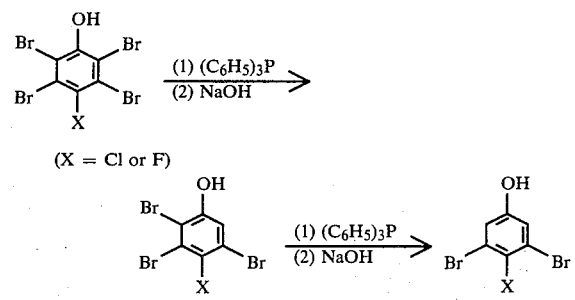

(X = Cl or F)

(3) According to the reaction scheme:

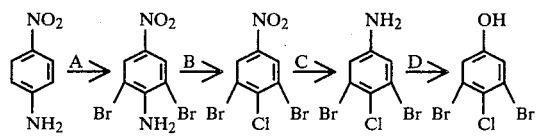

Step A according to Shepherd, J. Org. Chem. 12 (1947), 275, 281, steps B and C according to M. A. F. Hollemann, Rec. trav. chim. 37 (1917), 195, step D according to G. J. Tiessens, Rec. trav. chim. 50 (1931), 112.

(4) A very advantageous new method of obtaining 3,5-dibromo-4-chlorophenol, which also constitutes an object of the present invention, proceeds according to the reaction Scheme:

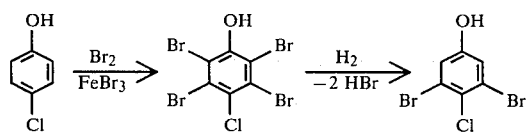

The bromination is carried out conventionally in accordance with e.g. the process mentioned in (1). The debromination is carried out catalytically using a hydrogenation catalyst in an organic solvent and in the presence of a strong base (preferably KOH, NaOH or sodium acetate). An excess of base is employed (preferably about 2 equivalents per equivalent of phenol). A suitable catalyst is preferably Raney nickel, Pd/carbon or Pd/CaCO$_3$. Suitable solvents are alcohols and cyclic ethers (e.g. ethanol, methanol, dioxane). Reference is also made in this connection to H. Kämmerer et al., Chem. Berichte 91 (1958), 1376 and M. Busch et al., Chem. Berichte 49 (1916), 1063.

3,5-Dichloro-4-bromophenol is particularly advantageously prepared by the following novel process, which likewise constitutes an object of the invention. In this process, 3,5-dichlorophenol is selectively brominated with bromine in the 4-position. The bromination is carried out in the presence of a Friedel-Craft catalyst, for example in the presence of ZnCl$_2$, AlBr$_3$ or preferably of AlCl$_3$. To increase the selectivity it is possible to use additionally diphenyl sulfide. Preferably the bromination is carried out in the presence of AlCl$_3$ and diphenyl sulfide. An inert, preferably anhydrous organic, e.g. aprotic, solvent, is used as reaction medium. Preferred solvents are anhydrous halogenated aliphatic hydrocarbons, e.g. dichloroethane, methylene chloride, tetrachloroethane, and also anhydrous ethers, such as diethyl ether.

A selective chlorination reaction with the above catalysts is described by W. D. Watson in Tetrahedron Letters 1976, 2591.

In the following directions for obtaining the active compounds and in the use examples, parts and percentages are by weight unless otherwise stated.

Manufacturing Direction A (a) 56 g of 4-fluorophenol are dissolved in 400 ml of dichloroethane and 1.5 g of iron powder are added to the solution. The mixture is heated to 60° C. and, with stirring, 352 g of bromine are added dropwise in the course of 1 hour. The temperature is kept for 2 hours at 60° C., then the reaction mixture is cooled to room temperature and poured into water with vigorous stirring. The brown precipitate is collected by suction, washed firstly with dichloroethane and then with water, and dried in vacuo. Recrystallisation from ethanol yields 170 g 2,3,5,6-tetrabromo-4-fluorophenol in the form of brown crystals with a melting point of 178°–180° C.

(b) 83.6 g of 2,3,5,6-tetrabromo-4-fluorophenol are dissolved in 270 g of benzene and, with stirring, 165.5 g of aluminium chloride are added to the solution. The reaction mixture is stirred for 4 hours at reflux temperature, then cooled and poured into ice-water and extracted with toluene. The toluene solution is extracted with 2 N sodium hydroxide, the alkaline aqueous solution is neutralised with acid and extracted once more than toluene. The second toluene extract is washed, dried and concentrated, affording 48.4 g of dark crystals, which are subsequently recrystallised twice from cyclohexane. Yield: 29 g of 3,5-dibromo-4-fluorophenol in the form of brownish crystals with a melting point of 93°–95° C.

3,5-Dibromo-4-chlorophenol with a melting point of 120°–122° C. is obtained by repeating the procedures described in (a) and (b) using 4-chlorophenol as starting material.

Manufacturing Direction B (a) 128.6 g of 4-chlorophenol are dissolved in 800 ml of dichloroethane. After addition of 1 g of iron powder, the mixture is heated to 60° C. and, with stirring, 704 g of bromine are added dropwise in the course of 1 hour. The temperature is kept for 2 hours at 60° C., whereupon a viscous suspension forms. This suspension is cooled to room temperature and, with vigorous stirring, poured into water. The precipitate is collected by suction, washed firstly with dichloroethane and then with water, and dried. Recrystallisation from alcohol/dioxane affords 380 g of 2,3,5,6-tetrabromo-4-chlorophenol in the form of brown crystals with a melting point of 210°–212° C.

(b) 8.9 g of 2,3,5,6-tetrabromo-4-chlorophenol are dissolved in a mixture of 40 ml of 1 N methanolic KOH and 60 ml of methanol and then 4 g of Raney nickel are added to the solution. Hydrogenation is carried out with hydrogen in a shaking apparatus for 4½ hours under normal pressure at 20° C. The uptake of hydrogen is 98% of theory. The catalyst is removed by filtration and the filtrate is concentrated. The residue is recrystallised twice from cyclohexane, affording 3.5 g of 3,5-dibromo-4-chlorophenol in the form of colourless crystals with a melting point of 121° C.

Manufacturing Direction C 81.5 g of 3,5-dichlorophenol and 2.5 g of diphenyl sulfide are dissolved in 1 liter of anhydrous ether. Then 2.5 g of anhydrous aluminium chloride are added and 80 g of bromine are added dropwise at room temperature in the course of 10 minutes. The reaction mixture is then stirred for 15 hours at reflux temperature and subsequently poured into water. The organic phase is separated, washed neutral with water, dried and concentrated. The solid residue is recrystallised from cyclohexane, affording 72.6 g of 3,5-dichloro-4-bromophenol in the form of colourless crystals with a melting point of 118°–120° C.

EXAMPLE 1

Test of the bactricidal and fungicidal activity of the halophenol compounds in the suspension test:

Each of a number of phosphate buffer media (pH 5, 7 and 8) containing, respectively, 1000, 100, 10, 1 or 0.1 ppm of 3,5-dibromo-4-chlorophenol, 3,5-dibromo-4-fluorophenol or 3,5-dichloro-4-bromophenol, is inoculated with a test strain (bacteria: O/n-cultures; fungi: spore suspension, 14-day cultures). Final concentration: $10^6$ bacilli/ml. The concentration at which the bacilli are killed is ascertained after an incubation of 18 hours at 20° C. on a magnetic stirrer. The compounds exhibit an excellent bactericidal activity in this test.

The test microorganisms are:
*Staph. aureus*—ATCC 6538
*E. choli*—ATCC 11229
*Ps. aeruginosa*—ATCC 15442
*Aspergillus niger*—ATCC 6275

Medium: phosphate buffer of Sörensen (1/15 molar) with 2% of brain heart infusion broth.

EXAMPLE 2

Test of the bactericidal and fungicidal activity of the trihalophenol compounds in the Agar Incorporation Test:

A 5% stock solution of each of 3,5-dibromo-4-chlorophenol, 3,5-dibromo-4-fluorophenol and 3,5-dichloro-4-bromophenol in ethylene glycol monomethyl ether is prepared. A dilution series is prepared from the stock solution, so that the concentration in each individual solution differs by a power of ten. Then 0.3 ml each of the solutions is put into a Petri dish and mixed with 15 ml of hot liquid nutrient medium (nutrient agar). The nutrient medium then contains 1000, 100, 10, 1 and 0.1 ppm respectively of active substance.

After the plates have congealed, the microorganism suspensions are dropped thereon with a Pasteur pipette or with the inoculation device (the microorganisms are the same as those employed in Example 1). Bacteria are incubated for 24 hours at 37° C., *Aspergillus niger* for 3 days at 28° C. Subsequently, the concentration of active compound up to which the bacilli have grown is determined. All three compounds exhibit a good bacteriostatic and fungistatic activity against the tested microorganisms.

EXAMPLE 3

3,5-Dibromo-4-chlorophenol, 3,5-dibromo-4-fluorophenol and 3,5-dichloro-4-bromophenol are each dissolved in a suitable formulation (ethylene glycol monoethyl ether/dimethyl formamide). The three textile substrates listed below are put into the formulation baths and subsequently squeezed out between 2 aluminium sheets. The substrates are the dried in the air. The squeezing is carried out such that 1000 ppm of active substance are present on the fabric.

1. Reinforced cotton, causticised, bleached, weight per m$^2$: 121 g
2. Polyamide, nylon staple fabric, fixed, bleached, weight per m$^2$: 140 g.
3. Polyester, "Dacron" [Registered Trade Mark] staple fabric, type 54, fixed, bleached, weight per m$^2$: 130 g.

The substrates are then tested against the following 7 test organisms according to the agar diffusion test (modified ATCC test method 90, 1970):
Bacteria
*Staphylococcus aureus* ATCC 6538
*Escherichia coli* NCTC 8196
*Proteus mirabilis* NCTC 8309
*Pseudomonas aeruginosa* NCTC 8060
Fungi
*Candida albicans* ATCC 10'259
*Trichophyton mentagrophytes* ATCC 9533
*Aspergillus niger* ATCC 6275

The test plates consist of a twin layer agar, i.e. of a base layer of uninoculated nutrient agar and a surface layer of inoculated nutrient agar.
Bacteria: nutrient agar, Fungi: mycophil agar The filtered micro-organism suspension is poured on a congealed base layer and after the inoculated layer has congealed, discs of the respective substrates of 20 mm diameter are placed on the treated substrates. The bacteria and candida plates are incubated for 24 hours at 37° C.; the fungi plates are incubated for 3 to 5 days at 28° C. After incubation the plates are evaluated for inhibition zones. If there are no inhibition zones, the growth beneath the test samples is examined under a magnifying glass.

The compounds tested in this manner exhibit, in conjunction with the substrates employed, good action against the above bacteria and fungi.

EXAMPLE 4

Crude paper which consists of 90% of bleached sulfite cellulose and 10% of birch is impregnated in a sizing press with a 0.25% solution of 3,5-dibromo-4-chlorophenol in methanol/water (2:1) to a pick-up of 40%. The dried paper contains 0.1% of active compound, based on its own weight.

To test the action against bacteria, discs of the impregnated paper measuring 10 mm in diameter are laid on brain heat infusion agar plates which have been inoculated beforehand with Staphylococcus aureus. The plates are then incubated for 24 hours at 37° C. To test the action against fungi, paper discs of 25 mm diameter are laid on mycophil agar plates and then inoculated with Aspergillus niger. The plates are then incubated for 72 hours at 30° C. On the one hand, the inhibition zones (IZ in mm) occurring around the paper discs are evaluated, and, on the other, the growth which can be determined microscopically (G in %) beneath or on the discs. The tested compounds exhibit good action against the bacteria employed.

Similar results are obtained using 3,5-dibromo-4-fluorophenol or 3,5-dichloro-4-bromophenol instead of 3,5-dibromo-4-chlorophenol.

EXAMPLE 5

The following mixture is rolled for 20 minutes at 150° C. on a two roll mill:
100 g of polyvinyl chloride,
19.20 g of di-(2-ethylhexylphthalate),
27 g of di-(2-ethylhexylsebacate),
1.50 g of Ba/Cd laurate,
0.25 g of stearic acid
3.10 g of 3,5-dibromo-4-chlorophenol, 3,5-dibromo-4-fluorophenol or 3,5-dichloro-4-bromophenol.

The roller nip is adjusted such that 1 mm rough sheets are produced. These sheets are then pressed for 20 minutes at 165° to 170° C. with a pressure of 1400 kg/cm$^2$.

To test the action against bacteria, round pieces measuring 10 mm in diameter are punched from the rolled plasticized polyvinyl chloride and laid on brain heart infusion agar plates which have been inoculated beforehand with Staphylococcus aureus. The plates are then incubated for 24 hours at 37° C. No growth of the test bacteria was observed beneath the discs.

EXAMPLE 6

A sample of 140 g of cotton/poplin is impregnated at 20° C. for 7 minutes in a bath of the following composition:
1000 ml of water
2.7 ml of an after-rinse liquor (containing 7% of a mixture of di-octadecyl- and di-hexadecyldimethylammonium chloride)
25 mg of 3,5-dibromo-4-chlorophenyl, 3,5-dibromo-4-fluorophenol or 3,5-dichloro-4-bromophenol.

The treated fabric is squeezed out to a pick-up of 100% and then dried at 45° C.

To test the action against bacteria, discs of the impregnated fabric measuring 25 mm in diameter are laid on brain heart infusion agar plates which have been inoculated with Staphylococcus aureus. The plates are incubated for 24 hours at 37° C. In all three cases no growth of the test bacteria was observed beneath the disc.

EXAMPLE 7

An emulsifiable concentrate is prepared by mixing the following constituents:
- 10 parts of 3,5-dibromo-4-chlorophenol, 3,5-dibromo-4-fluorophenol or 3,5-dichloro-4-bromophenol,
- 68 parts of xylene
- 10 parts of dimethyl formamide
- 12 parts of surfactant.

Before application, the concentrate is diluted with water to 50 to 500 times its volume. Wood, sawdust or cellulose fibres are immersed in the respective emulsion, whereby they are protected against attack by bacteria and fungi.

EXAMPLE 8

An oil-soluble concentrate is prepared by mixing the following constituents:
- 20 parts of 3,5-dibromo-4-chlorophenol, 3,5-dibromo-4-fluorophenol or 3,5-dichloro-4-bromophenol
- 40 parts of ethylene glycol monoethyl ether
- 10 parts of dimethyl formamide
- 30 parts of xylene This concentrate is mixed with a paint or cutting oil, such that the paint or oil contains 0.1% of trihalophenol and is thereby protected against attack by bateria and fungi.

EXAMPLE 9

A wettable powder is prepared by mixing the following constituents:
- 55 parts of 3,5-dibromo-4-chlorophenol, 3,5-dibromo-4-fluorophenol or 3,5-dichloro-4-bromophenol
- 3 parts of polyethylene oxide
- 5 parts of ligninsulfonic acid
- 20 parts of diatomaceous earth
- 17 parts of clay.

The powder is suspended in water and sprayed in animal stables to inhibit the growth of fungi and bacteria.

EXAMPLE 10

A concentrate formulated according to Example 7 is diluted with water to 10 to 100 times its volume and added to the recirculating water in a machine for paper manufacturing, such that the concentration of trihalophenol is 10 to 200 ppm. The formation of slime that would otherwise occur is effectively inhibited.

EXAMPLE 11

An emulsifiable concentrate formulated according to Example 7 is diluted with water to 400 to 800 times its volume. Rectangular test samples of birch wood measuring 5 cm×5 mm are immersed for 2 minutes in the respective emulsion and dried for 24 hours at room temperature. The samples are then laid on the surface of agar plates. Spore suspension of *Aspergillus niger* are sprayed onto the plates and the samples. The fungi are incubated for 2 weeks at 95% relative humidity and 28° C. Compared with untreated samples, a pronounced inhibition of the growth of the test microorganisms is observed.

EXAMPLE 12

(a) 8.95 g of 3,5-dibromo-4-chlorophenol or 3,5-dichloro-4-bromophenol are dissolved in 120 ml of ethylene glycol monoethyl ether and the solution is stirred into an aqueous mixture which contains 150 g of a water-repellent agent based on a paraffin emulsion containing zirconium salt, and 1.5 ml of 80% acetic acid. The suspension is bulked with water to 1 liter.

(b) 8.95 g of 3,5-dibromo-4-chlorophenol or 3,5-dichloro-4-bromophenol are dissolved in 120 ml of ethylene glycol monoethyl ether and the solution is stirred into an aqueous mixture which contains 50 g of a water-repellent agent based on hexamethylolmelamine ether modified with stearic acid and triethanolamine, combined with paraffin, 6.3 ml of acetic acid and 2.5 g of aluminum sulfate (57–60%). The suspension is bulked with water to 1 liter.

Pieces of cotton, cotton/polyester (67/33) and polyacrylonitrile fabric are padded with the suspension obtained in (a) and (b) to a liquor pick-up of 70%, then dried for 10 minutes at 120° C., condensed for 4½ minutes at 150° C. and allowed to condense overnight at room temperature.

After they have been subjected to a spray test and xenon light test, the pieces of fabric undergo a mildew resistance test (DIN 53 931). The bacilli employed are: *Aspergillus niger* ATCC 6275, *Chaetomium globosum* ATCC 6205 and *Penicillium funiculosum* ATCC 9644. Oatmeal-malt agar and mineral salt-cellulose agar are used as nutrient media. The test demonstrates that 3,5-dibromo-4-chlorophenol and 3,5-dichloro-4-bromophenol effect a very good mildew-resistant action on the treated fabrics.

What is claimed is:

1. A method of protecting organic and inorganic material from attack by micro-organisms, which comprises incorporating in or applying to the surface of said material 3,5-dibromo-4-chlorophenol, 3,5-dibromo-4-fluorophenol or 3,5-dichloro-4-bromophenol or a mixture thereof, an amount of about 100 to 10,000 ppm based on the material to be protected.

2. A method according to claim 1 for protecting substrates of organic origin from rot and mildew induced by fungi and bacteria.

3. A method according to claim 1 for protecting technical formulations and plastics moulding compounds from attack by bacteria and fungi.

4. A method according to claim 1 for protecting paper-making slurries and machines used in the paper industry from the formation of slime induced by microorganisms.

5. A method according to either of claim 3 or 4, which comprises incorporating in the substrates to be protected 100 to 10,000 ppm, preferably 200 to 5000 ppm, of a trihalophenol compound as defined in claim 1.

6. A method according to claim 2 for protecting wood, wood shavings and sawdust from attack by fungi and bacteria.

7. A method according to claim 6, which comprises applying 0.1 to 10 g of trihalophenol compound per square meter to the wood.

8. A method according to claim 2 for protecting textiles from attack by microorganisms.

9. A method according to claim 8 for protecting textiles made from natural fibres, preferably cellulose fibres, from bacteria and fungi that cause rot, and also from mildew.

10. A method according to claim 8, which comprises impregnating the textiles by the pad or exhaust method with a solution or dispersion which contains the trihalophenol compound and which can additionally contain assistants conventionally employed in the dyeing industry.

11. A method according to claim 10, which comprises applying the trihalophenol compound to the textile fabric in an amount of 100 to 5000 ppm, preferably 200 to 2000 ppm, based on the weight of said fabric.

12. A method according to claim 1, wherein the trihalophenol compound is 3,5-dibromo-4-chlorophenol or 3,5-dichloro-4-bromophenol.

* * * * *